(12) United States Patent
Konishi et al.

(10) Patent No.: US 11,152,104 B2
(45) Date of Patent: Oct. 19, 2021

(54) MEDICAL DATA MANAGING APPARATUS AND MEDICAL DATA MANAGING SYSTEM

(71) Applicant: CANON MEDICAL SYSTEMS CORPORATION, Otawara (JP)

(72) Inventors: Hayato Konishi, Otawara (JP); Yasuyuki Miyoshi, Nasushiobara (JP); Keita Mitsumori, Nasushiobara (JP); Yosuke Yanagida, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 551 days.

(21) Appl. No.: 15/869,693

(22) Filed: Jan. 12, 2018

(65) Prior Publication Data

US 2018/0204639 A1    Jul. 19, 2018

(30) Foreign Application Priority Data

Jan. 13, 2017  (JP) .............................. JP2017-003968

(51) Int. Cl.
*A61B 5/00* (2006.01)
*G16H 30/20* (2018.01)
(Continued)

(52) U.S. Cl.
CPC ............. *G16H 30/20* (2018.01); *G06F 21/32* (2013.01); *G06F 21/6245* (2013.01);
(Continued)

(58) Field of Classification Search
CPC .................. G06F 15/16; G06F 17/30
(Continued)

(56) References Cited

U.S. PATENT DOCUMENTS

| | | | |
|---|---|---|---|
| 7,769,602 B2* | 8/2010 | Motoki | G16H 10/60 705/3 |
| 8,478,842 B2* | 7/2013 | Holmes | G06F 19/321 709/219 |

(Continued)

FOREIGN PATENT DOCUMENTS

JP      2003-248723      9/2003

OTHER PUBLICATIONS

Google patents search, Feb. 29, 2020 (Year: 2020).*
Google patents search, Jun. 9, 2021 (Year: 2021).*
ip.com search, Jun. 9, 2021 (Year: 2021).*

*Primary Examiner* — Dilek B Cobanoglu
(74) *Attorney, Agent, or Firm* — Oblon, McClelland, Maier & Neustadt, L.L.P.

(57) ABSTRACT

A medical data managing apparatus includes processing circuitry. The processing circuitry generates network access data based on patient information of a patient. The processing circuitry acquires the reference data from a data generating device via a communication network constructed based on the network access data, and checks the reference data against benchmark data included in the patient information. The processing circuitry acquires, when it is determined that the reference data and the benchmark data represent same patient as a result of the check, the multiple non-DICOM data from the data generating device via the constructed communication network. The processing circuitry classifies each of the multiple non-DICOM data into first non-DICOM data to be registered in a data archive apparatus or other second non-DICOM data, and displays the first non-DICOM data and the second non-DICOM data on a display in different display modes.

21 Claims, 13 Drawing Sheets

(51) Int. Cl.
*G16H 10/60* (2018.01)
*G06F 21/62* (2013.01)
*G06K 9/62* (2006.01)
*H04L 29/08* (2006.01)
*G06F 21/32* (2013.01)
*G06K 9/00* (2006.01)
*H04L 12/46* (2006.01)

(52) U.S. Cl.
CPC ........... *G06K 9/6267* (2013.01); *G16H 10/60* (2018.01); *H04L 67/02* (2013.01); *G06K 9/00255* (2013.01); *G06K 9/00288* (2013.01); *G06K 9/6201* (2013.01); *H04L 12/4641* (2013.01)

(58) Field of Classification Search
USPC ............... 709/219; 707/736; 358/403; 705/3
See application file for complete search history.

(56) References Cited

U.S. PATENT DOCUMENTS

2014/0317109 A1* 10/2014 Romatoski ............ G06F 19/321
707/736
2016/0042229 A1* 2/2016 Liao ..................... G06K 9/2054
358/403

* cited by examiner

LIST INCLUDING PATIENT INFO

| | NAME | ID | HEIGHT (mm) | WEIGHT (kg) | BENCHMARK DATA | | | |
| --- | --- | --- | --- | --- | --- | --- | --- | --- |
| | | | | | FACE IMAGE DATA | INSURANCE CARD IMAGE DATA | CONSULTATION TICKET IMAGE DATA | BAR CODE DATA |
| PATIENT INFORMATION A | T TARO | A01 | 1850 | 80 |  | T TARO .... | T TARO .... | XXXXXXXXXXXXX |
| PATIENT INFORMATION B | J HANAKO | A02 | 1580 | 48 |  | J HANAKO .... | J HANAKO .... | YYYYYYYYYYYY |
| PATIENT INFORMATION C | I JIROU | A22 | 1740 | 75 |  | I JIROU .... | I JIROU .... | ZZZZZZZZZZZZ |
| ... | ... | ... | ... | ... | ... | ... | ... | ... |

FIG. 7

MEDICAL DATA MANAGING APPARATUS AND MEDICAL DATA MANAGING SYSTEM

CROSS-REFERENCE TO RELATED APPLICATION

This application is based upon and claims the benefit of priority from Japanese Patent Application No. 2017-003968, filed on Jan. 13, 2017, the entire contents of each of which are incorporated herein by reference.

FIELD

An embodiment as an aspect of the present invention relates to a medical data managing apparatus and a medical data managing system.

BACKGROUND

Medical institutions (for example, a radiology institution) managing DICOM (Digital Imaging and Communications in Medicine) data in a medical institution such as a hospital own a medical image data system (PACS: Picture Archiving and Communication System) that is an archive system for efficiently managing and storing DICOM data. The DICOM is a standard that defines a communication protocol between a format of a medical image data, acquired by a medical image diagnostic device such as an X-ray CT (Computed Tomography) device or an MRI (Magnetic Resonance Imaging) device, and a medical imaging device handling the medical image data.

The other institution in the medical institution manages and stores non-DICOM data efficiently. The non-DICOM data is, for example, image data such as JPG format or PNG format taken with a general optical camera, data in text format including character data or HTML (Hyper-Text Markup Language) format, moving image data such as MPEG format, or waveform data such as electrocardiogram.

In such a medical institution, there is a need for a system that is able to centrally manage medical data and to be listed for each patient, regardless of whether it is the DICOM data or the non-DICOM data. The need to utilize a system for regional medical cooperation is increasing. This system not only manages or stores medical data of one medical institution but also centrally manages multiple medical data over multiple medical institutions and also operates the multiple medical data with a common rule.

In view of this, VNA (Vendor Neutral Archive) which is an archive system capable of collectively managing various data managed by the PACS of different makers and each clinical department system, has attracted attention and spreading. The VNA associates the non-DICOM data with patient information such as patient name and registers it.

BRIEF DESCRIPTION OF THE DRAWINGS

In accompanying drawings,

FIG. 7 a diagram for explaining a list screen and a registration result in the medical data managing apparatus according to the first embodiment;

DETAILED DESCRIPTION

A medical data managing apparatus and a medical data managing system according to embodiments will be described in detail with reference to the drawings.

The medical data managing apparatus according to the embodiment is connected via a communication network to a data generating device owning reference data for verification and multiple non-DICOM data and to a data archive apparatus. The medical data managing apparatus includes processing circuitry. The processing circuitry generates network access data based on patient information of a patient. The processing circuitry acquires the reference data from the data generating device via a communication network constructed based on the network access data, and checks the reference data against benchmark data included in the patient information. The processing circuitry acquires, when it is determined that the reference data and the benchmark data represent same patient as a result of the check, the multiple non-DICOM data from the data generating device via the constructed communication network. The processing circuitry classifies each of the multiple non-DICOM data into first non-DICOM data to be registered in the data archive apparatus or other second non-DICOM data, and displays the first non-DICOM data and the second non-DICOM data on a display so as to be recognizable from each other.

1. First Embodiment

Figure 1:
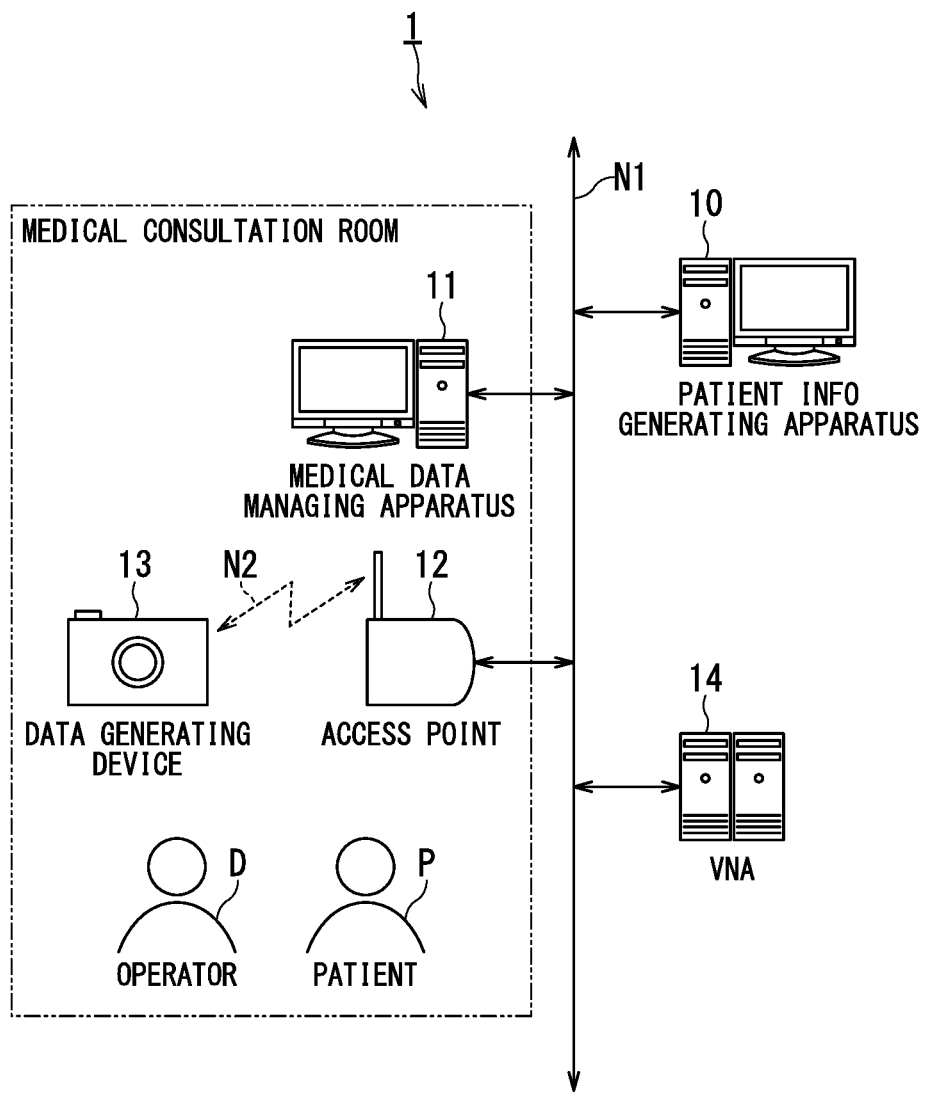
FIG. 1 is a schematic diagram showing the overall configuration of a medical data managing system according to a first embodiment.

FIG. 1 is a schematic diagram showing the overall configuration of a medical data managing system according to a first embodiment.

FIG. 1 shows a medical data managing system 1 according to the first embodiment. The medical data managing system 1 includes a patient information generating apparatus 10, a medical data managing apparatus 11, an access point (wireless LAN access point) 12, a data generating device (for example, an optical camera) 13, and a VNA 14. The patient information generating apparatus 10, the medical data managing apparatus 11, the access point 12, and the VNA 14 are mutually connectable via a communication network N1 such as a wired LAN (Local Area Network). The data generating device 13 can be mutually connected to the access point 12 via a communication network N2 such as a wireless LAN.

The medical data managing apparatus 11, the access point 12, and the data generating device 13 are provided in a medical consultation room where an operator D such as a doctor and the patient P are present. The operator D examines the patient P in the medical consultation room and instructs registration of non-DICOM data related to the patient P. The patient P is a person who consults the operator D in the medical consultation room and has patient information associated with the non-DICOM data instructed to be registered by the operator D.

The patient information generating apparatus 10 includes hospital information systems (HIS), radiology information systems (RIS), a medical reception apparatus, a medical image diagnostic device, an electronic medical chart server, a modality work-list management (MWM) server, and the like. The medical reception apparatus is, when receiving a medical treatment request from the patient, a device for generating a reception data including the patient information. The medical image diagnostic device is a device for generating a file of a medical image including the patient information, and includes, for example, devices such as an X-ray CT device, an MRI device, and an ultrasonic diagnostic device. The electronic medical chart server owns an electronic medical chart including the patient information, and provides the electronic medical chart in response to a request from a client. The MWM server is a server that delivers reservation data (order) of examination including the patient information to the medical image diagnostic device. The patient information generating apparatus 10 generates the patient information. The patient information generating apparatus 10 transmits the patient information to the medical data managing apparatus 11 via the communication network N1.

Figure 2:
FIG. 2 is a diagram showing an example of a list including patient information in the medical data managing system according to the first embodiment.
Figure 2:
Figure 2:

FIG. 2 is a diagram showing an example of a list Including patient information in the medical data managing system 1.

As shown in FIG. 2, the list includes the patient information related to the respective patients. Each of pieces of the patient information includes name (patient name), ID (Identification), height, weight, benchmark data, and the like of the patient. The benchmark data includes image data, bar code data, and the like. The image data indicates data acquired as an image, and includes image data such as face image data, insurance card image data and consultation ticket image data acquired by an optical camera, and image data based on biological data such as a fingerprint. The face image data is image data acquired by photographing a face of each patient. The insurance card image data is image data acquired by photographing an insurance card carried by each patient. The consultation ticket data is an image data acquired by photographing a consultation ticket carried by each patient. The bar code data is data indicating numerical values and characters identified by a bar code (striped pattern) for identifying each patient.

Figure 3:
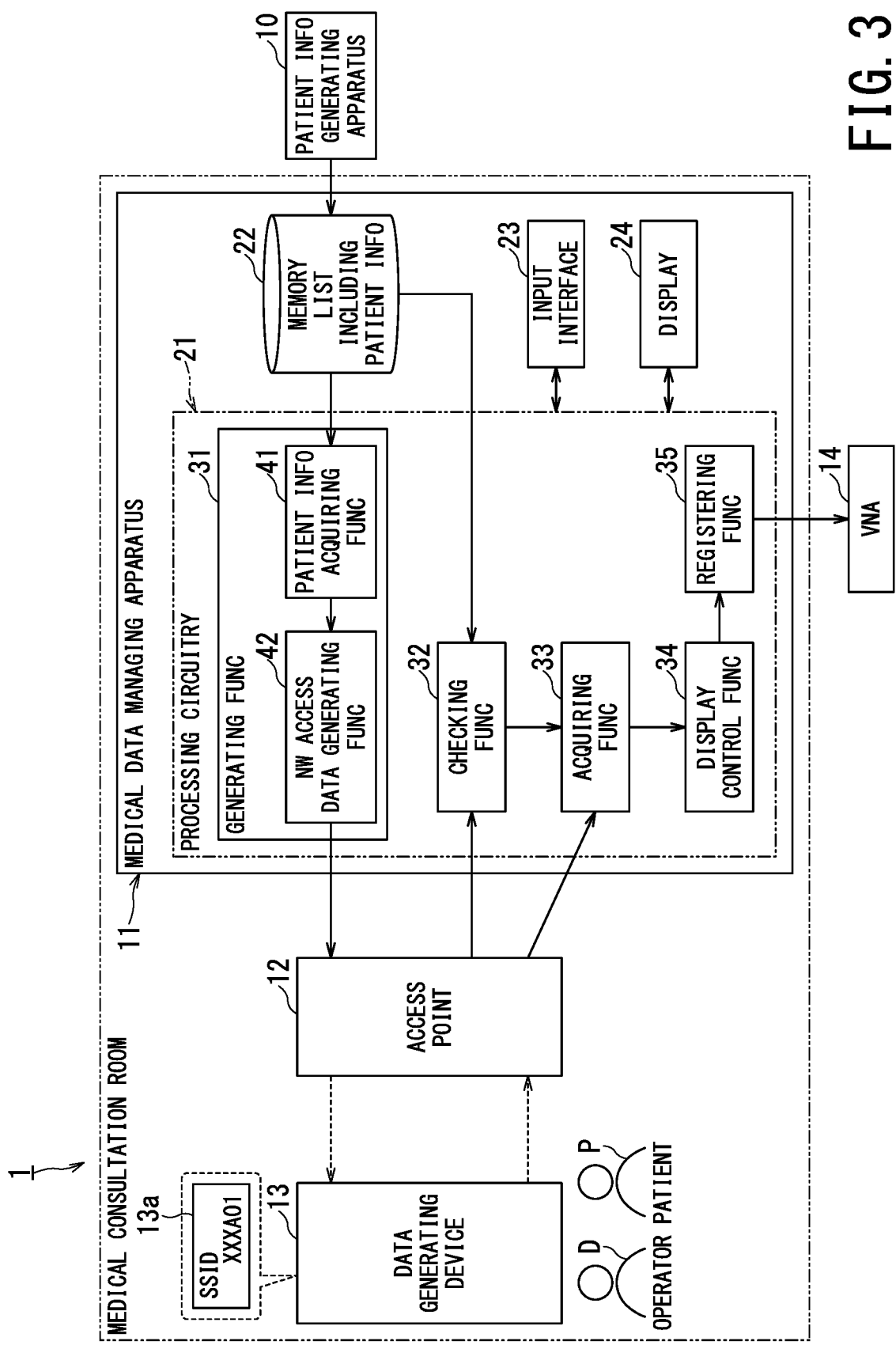
FIG. 3 is a diagram for explaining configurations and functions of the medical data managing system according to the first embodiment.

FIG. 3 is a diagram for explaining configurations and functions of the medical data managing system 1.

The medical data managing apparatus 11 includes processing circuitry 21, a memory (or storage) 22, an input interface 24, and a display 24.

The processing circuitry 21 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 21 realizes functions to be described later by reading out and executing a program stored in the memory 22 or directly incorporated in the processing circuitry 21.

The processing circuitry 21 may be a single processing circuit or a combination of multiple processing circuits. In the latter case, the memory 22 includes multiple memory elements each storing an element of a program that the processing circuitry 21 executes, and each corresponding to the processing circuit. Alternatively, in the latter case, the memory 22 includes a single memory storing the program that the processing circuitry 21 executes, and corresponding to the multiple processing circuits.

The memory 22 includes a semiconductor memory element such as a random access memory (RAM), a flash memory and the like, a hard disk, an optical disk and the like. The memory 22 may be a portable media such as a universal serial bus (USB) memory, a digital video disk (DVD) and the like. The memory 22 stores various processing programs (in addition to application programs, an operating system (OS) and the like are also included), data required for execution of the programs, and medical images used in the processing circuitry 21. The OS may include a graphical user interface (GUI) which enables basic operations by the input interface 23 by using many graphics in display of information on the display 24 to the operator D.

The memory 22 stores a list (shown in FIG. 2) including the patient information. The list including the patient information is transmitted from the patient information generating apparatus 10 such as the medical reception apparatus.

The input interface 23 is a circuit inputting a signal from an input device, and also includes the input device itself. The input device includes a pointing device (a mouse and the like), a keyboard, various buttons and the like. When the input device is operated by the operator D, the input interface 23 generates an input signal according to the operation and outputs it to the processing circuitry 21. The medical data managing apparatus 11 may include a touch panel in which the input device is constituted integrally with the display 24.

The display 24 is a display device such as a liquid crystal display panel, a plasma display panel, and an organic EL (Electro Luminescence) panel.

When the processing circuitry 21 of the medical data managing apparatus 11 executes the program, a generating unit (generating function) 31, a checking unit (checking function) 32, an acquiring unit (acquiring function) 33, a display control unit (display control function) 34, and a registering unit (registering function) 35 are realized. All or part of the functions 31 to 35 may be provided as hardware in the medical data managing apparatus 11.

The generating function 31 includes a patient information acquiring function 41 and a network access data generating function 42. The patient information acquiring function 41 includes a function of acquiring the patient information (for example, patient ID) generated in the patient information generating apparatus 10 and stored in the memory 22. An example of the patient information is as described above with reference to FIG. 2.

The network access data generating function 42 includes a function of generating network access data based on the patient information acquired by the patient information acquiring function 41, and of providing the data generating device 13 with the network access data via the access point 12. For example, the network access data generating function 42 generates a service set identifier (SSID) as the network access data. The SSID is an identification name of the access point 12 when the communication network N2 is WiFi.

The checking function 32 includes a function of acquiring reference data from the data generating device 13 via the communication network N2 constructed based on the network access data. The checking function 32 is a function of checking the acquired reference data against the benchmark data included in the patient information acquired by the patient information acquiring function 41.

The acquiring function 33 includes a function of acquiring, when it is determined that the reference data and the benchmark data represent same patient as a result of checking by the checking function 32, multiple non-DICOM data from the data generating device 13 via the communication network N2. Here, the multiple non-DICOM data mean multiple datasets, and include non-DICOM data to be registered into the VNA 14 (hereinafter referred to as "first non-DICOM data") and other non-DICOM data (hereinafter referred to as "second non-DICOM data").

The display control function 34 includes a function of classifying each of the multiple non-DICOM data acquired by the acquiring function 33 into the first non-DICOM data or the second non-DICOM data, and of displaying the first non-DICOM data and the second non-DICOM data on the display 24 so as to be recognizable from each other.

The registering function 35 includes a function of registering registering-target non-DICOM data to be registered into the VNA 14, which is a part of the multiple non-DICOM data acquired by the acquiring function 33. The registering function 35 preferably includes a function of registering the registering-target non-DICOM data into the VNA 14 in association with the patient information.

For example, the registering function 35 may, based on a selecting operation by the operator D or a registration manager, (A) register all of multiple first non-DICOM data into the VNA 14 as the registering-target non-DICOM data, (B) register only a part of multiple first non-DICOM data into the VNA 14 as the registering-target non-DICOM data, (C) register the first non-DICOM data and a part of multiple second non-DICOM data into the VNA 14 as the registering-target non-DICOM data, or (D) register a part of multiple first non-DICOM data and a part of multiple second non-DICOM data into the VNA 14 as the registering-target non-DICOM data. The selecting operation of the registering-target non-DICOM data by the operator D or the registration manager is performed, for example, by a list screen (shown in FIG. 7) displayed by the display control function 34.

Details of the above-described functions 31 to 35 will be described later with reference to FIGS. 4 to 6.

The access point 12 is a wireless device that connects the data generating device 13 as a wireless LAN client (wireless terminal) to the communication network N1.

The data generating device 13 is a wireless LAN client such as a notebook computer, a smart-phone, or an optical camera, including a display 13*a*. Here, the non-DICOM data includes, for example, image data such as a JPG format and a PNG format photographed by a general optical camera, data such as text format and HTML format including character data, moving image data such as MPEG format Data, and waveform data such as an electrocardiogram. An owner of the data generating device 13 may be the operator D or the patient P in some cases. When the owner of the data generating device 13 is the patient P, the patient P brings it, in which the non-DICOM data has been generated and stored, to the medical consultation room at the time of his/her consultation. Hereinafter, a case where the data generating device 13 is the optical camera is described unless otherwise mentioned.

The VNA 14 is a type of a data archive apparatus that centrally stores and manages the DICOM data and the non-DICOM data. The VNA 14 is an archive system capable of collectively managing the non-DICOM data generated by the optical camera 13 and associated with appropriate patient information under a control of the medical data managing apparatus 11. The association between the non-DICOM data and the patient information may be made by tagging the patient information in a data file of the non-DICOM data, or performed by separately storing a table in which the non-DICOM data and the patient information are associated.

Subsequently, an operation of the medical data managing system 1 will be described with reference to FIGS. 4 to 6.

Figure 4:
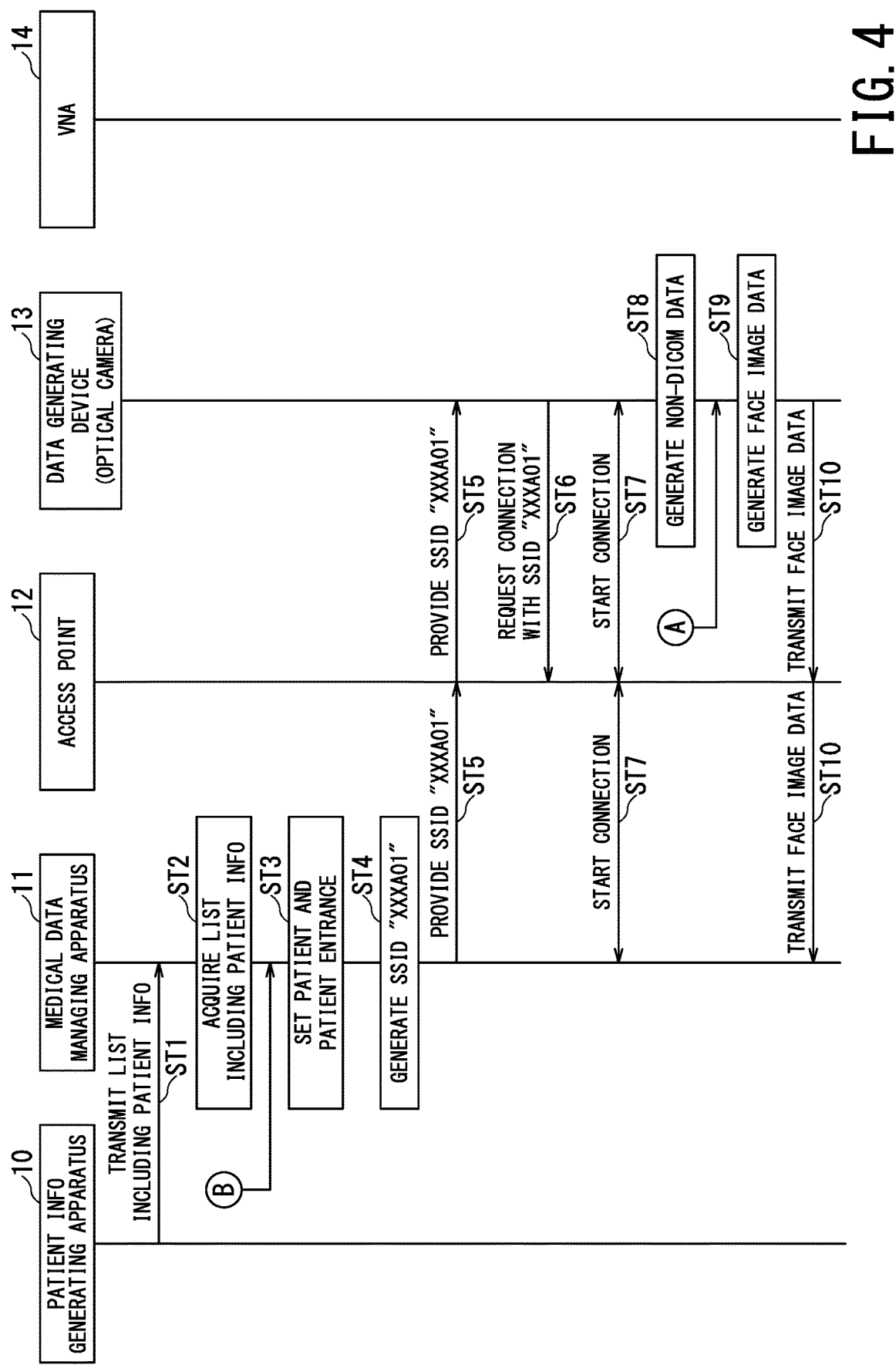
FIG. 4 is a flowchart showing a part of an operation example of the medical data managing system according to the first embodiment.
Figure 5:
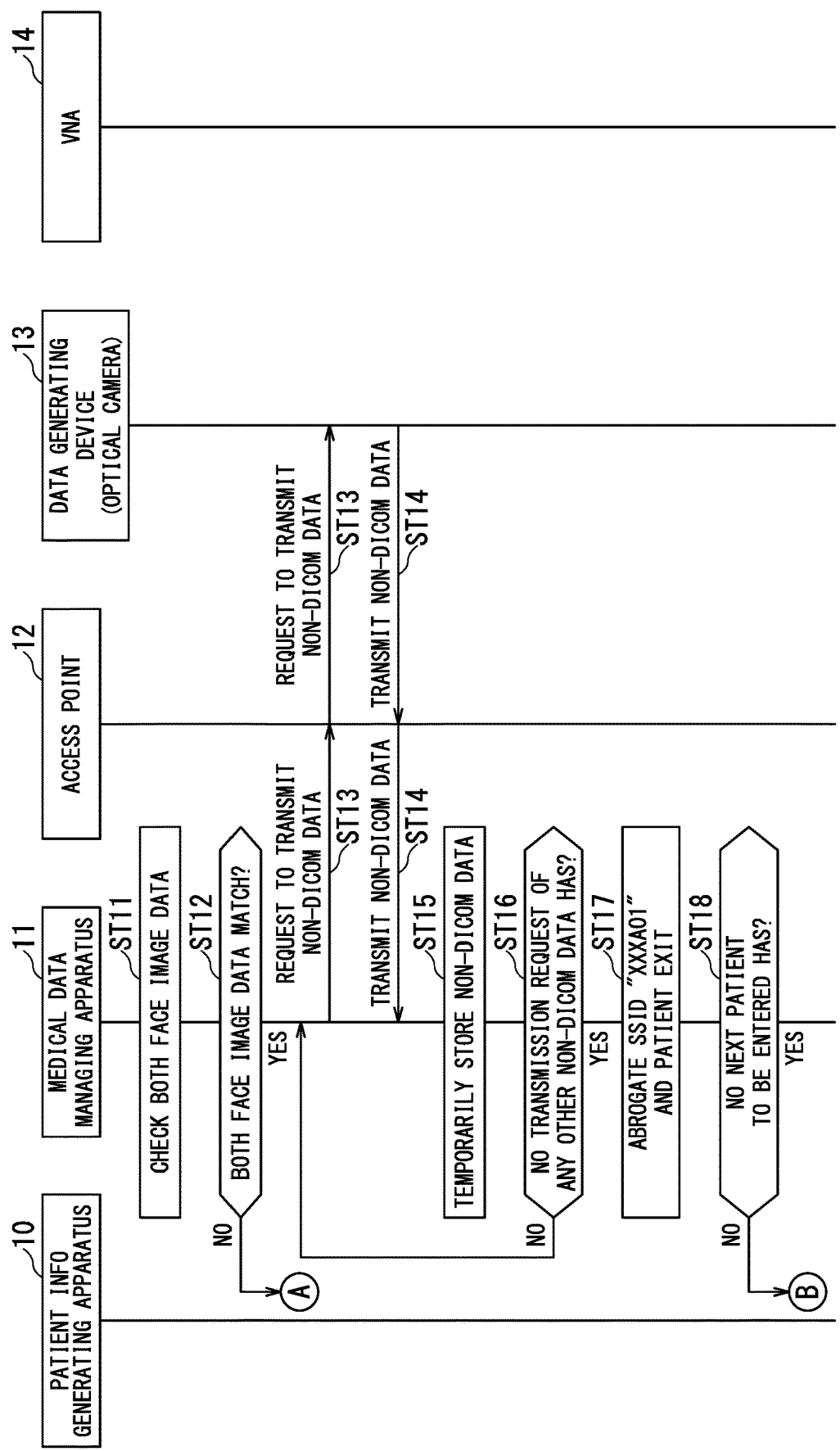
FIG. 5 is a flowchart showing a part of the operation example of the medical data managing system according to the first embodiment.
Figure 6:
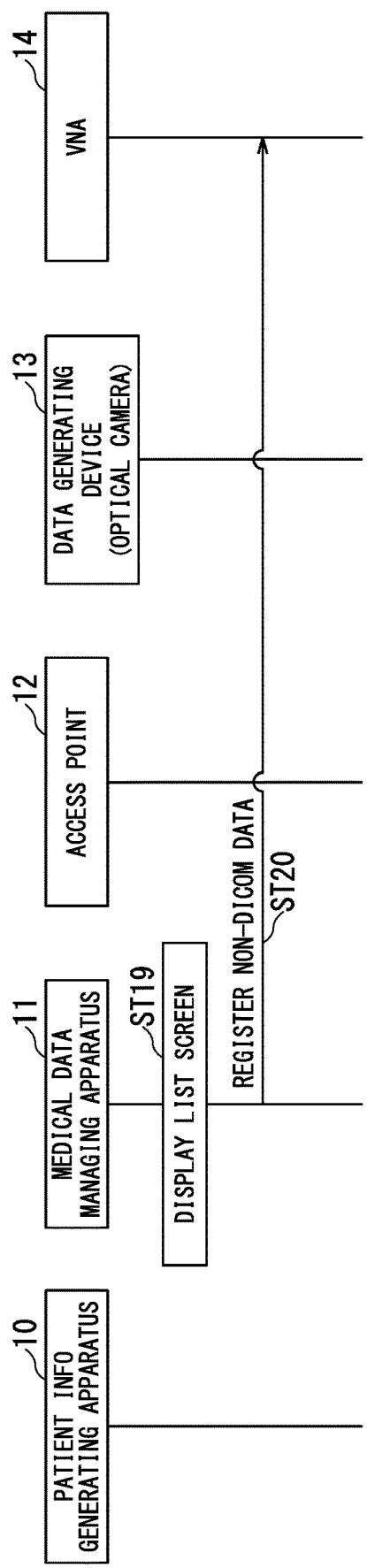
FIG. 6 is a flowchart showing a part of the operation example of the medical data managing system according to the first embodiment.

FIGS. 4 to 6 are a flowchart showing an operation example of the medical data managing system 1.

The operation of the medical data managing system 1 shown in FIGS. 4 to 6 is performed in order to register the registering-target non-DICOM data into the VNA 14 in association with the appropriate patient information, when the registering-target among the multiple non-DICOM data, stored in the optical camera 13, is registered into the VNA 14. Since the patient information is not originally associated with the multiple non-DICOM data stored in the optical camera 13, in the prior art, the operator has performed the association by manual operations.

As shown in FIG. 4, the patient information generating apparatus 10 such as the HIS transmits the list including the patient information (shown in FIG. 2) to the medical data managing apparatus 11 via the communication network N1 (step ST1).

The medical data managing apparatus 11 acquires the list including the patient information transmitted in step ST1 and stored in the memory 22 (step ST2). The medical data managing apparatus 11 sets a predetermined patient P out of the list including the patient information acquired in step ST2, and a patient P enters the medical consultation room according to an instruction of the operator D (step ST3). The setting of the patient P may be automatically performed so as to prioritize the superior of the list, or may be arbitrarily set by selection of the operator D.

Alternatively, the setting of the patient P may be performed by a manual input of the operator D to the medical data managing apparatus 11, regardless of the list. Hereinafter, in step ST3, a case where the medical data managing apparatus 11 sets the patient name "T Taro" that is the upper level of the list shown in FIG. 2 as the patient P, and where the patient P corresponding to the patient name "T Taro" enters will be described.

The medical data managing apparatus 11 generates an SSID of the access point 12 as the network access data based on the patient information on the patient P with the patient name "T Taro" set in step ST3 (step ST4). In step ST4, the medical data managing apparatus 11 generates the SSID including "A01" based on the ID "A01" as the patient information on the patient P with the patient name "T Taro".

For example, in step ST4, the medical data managing apparatus 11 generates, as the SSID including "A01", an SSID "A01" including only the ID "A01", an SSID "XXXA01" including the default "XXX" and the ID "A01". Hereinafter, the case where the medical data managing apparatus 11 generates the SSID "XXXA01" including the default "XXX" and ID "A01" in step ST4 will be described.

The medical data managing apparatus 11 provides the optical camera 13 with the SSID "XXXA01" generated in step ST4 via the access point 12 (step ST5). On the display 13a (shown in FIG. 3) of the optical camera 13, the SSID "XXXA01" is displayed. Any access point other than the access point 12 is preferably set to a stealth mode. By using a serial number or the like of the optical camera 13, a device accessible to the network may be limited in advance.

The operator D compares the ID "A01", related to the patient P of the patient name "T Taro" set on the display 24 set in step ST3, and the SSID "XXXA01" of the access point 12, displayed on the display 13a of the optical camera 13, the patient P being in the medical consultation room. As a result of the comparison, the operator D determines that the ID "A01", related to the patient P of the patient name "T Taro" in the medical consultation room, matches an ID portion "A01" of the SSID "XXXA01" of the access point 12.

The optical camera 13 requests a connection to the access point 12 with the SSID "XXXA01" by an operation of the operator D (step ST6). As a result, the optical camera 13 is connected to the medical data managing apparatus 11 via the communication network N2 constructed based on the SSID "XXXA01" (step ST7).

According to the connection in steps ST4 to ST7 described above, appropriateness of the patient information to be associated with the non-DICOM data is, when connecting the optical camera 13 to the medical data managing apparatus 11, is assigned to the operator D using the SSID. Therefore, when the optical camera 13 is connected to the medical data managing apparatus 11, it is possible to prevent mistakes in the patient information at the time of the association, which was a problem in the conventional technique.

Following step ST7, the operator D uses the optical camera 13 to photograph an object such as an affected part of the patient P with the patient name "T Taro" who is in the medical consultation room, and as a result, the optical camera 13 generates multiple non-DICOM data related to the patient P with the patient name "T Taro" (step ST8). It should be noted that the step ST8 may be performed before the communication network N2 is constructed in step ST7.

The operator D uses the optical camera 13 to photograph a face of the patient P with the patient name "T Taro" who is in the medical consultation room, and as a result, the optical camera 13 generates face image data related to the patient P with the patient name "T Taro" (step ST9). Here, the operator D uses, when the reference data shown in FIG. 2 is bar code data, a bar code reader function of the optical camera 13 to read a bar code of a ribbon attached to a wrist of the patient P with the patient name "T Taro" who is in the medical consultation room, and as a result, the optical camera 13 generates the bar code data related to the patient P with the patient name "T Taro" (step ST9).

The optical camera 13 transmits the face image data, related to the patient P with the patient name "T Taro" generated in step ST9, to the medical data managing apparatus 11 via the communication network N2 constructed based on the SSID "XXXA01" and the communication network N1 (step ST10).

Turning to the explanation of FIG. 5, the medical data managing apparatus 11 checks the face image data transmitted in step ST10 against the face image data included in the patient information relating to the patient name "T Taro" set in step ST3 (step ST11). Here, the checking of two face image data can be realized by, for example, a pattern matching using feature point extraction (including character string matching), or the like.

The medical data managing apparatus 11 determines whether or not the face image data transmitted in step ST10 matches the face image data set in step ST3, or whether or not both face image data represent same patient (step ST12). That is, the medical data managing apparatus 11 matches the face image data, corresponding to the non-DICOM data relating to the patient in the medical consultation room, with the face image data, included in the patient information to be associated with the non-DICOM data, as a result, it is determined whether or not the non-DICOM data should be associated with the patient information.

If it is determined as YES in step ST12, that is, if it is determined that the transmitted face image data matches the face image data included in the patient information, the medical data managing apparatus 11 requests the optical camera 13 to transmit the non-DICOM data via the communication networks N1 and N2 (step ST13).

If it is determined as NO in step ST12, that is, if it is determined that the transmitted face image data does not match the face image data included in the patient information, the medical data managing apparatus 11 notifies that fact to the optical camera 13. Then, the optical camera 13 again generates face image data on the patient P with the patient name "T Taro" as the reference data (step ST9 in FIG. 4).

Following step ST13, the optical camera 13 transmits, in accordance with an operation of the operator D, the non-DICOM data generated in step ST8 to the medical data managing apparatus 11 via the communication networks N2 and N1 (step ST14). Here, the optical camera 13 may perform a predetermined process on the non-DICOM data, and transmit the processed non-DICOM data to the medical data managing apparatus 11 via the communication networks N2 and N1. The predetermined processing includes an encryption processing for securing security, a compression processing for reducing data size, and the like. The optical camera 13 applies at least one of the encryption processing and the compression processing to the non-DICOM data.

The medical data managing apparatus 11 is able to determine, when the non-DICOM data is transmitted from the optical camera 13, the suitability of the patient information to associate with the non-DICOM data generated by the optical camera 13, as shown in steps ST9 (shown in FIG. 4) to ST14. Therefore, it is possible to prevent mistakes in the patient information at the time of the association, which was a problem in the conventional technique, when the optical camera 13 is connected to the medical data managing apparatus 11 (steps ST4 to ST7) and when the non-DICOM data is transmitted (steps ST10 to ST14).

The medical data managing apparatus 11 receives the non-DICOM data transmitted in step ST14, and temporarily stores the non-DICOM data into the memory 22 in association with the patient information corresponding to the SSID "XXXA01" generated by step ST4 (shown in FIG. 4) (step ST15). Here, the medical data managing apparatus 11 performs, when the non-DICOM data subjected to the encryption process is received from the optical camera 13, a decryption process on the encrypted non-DICOM data and makes the correspondence. The medical data managing apparatus 11 performs, when the non-DICOM data subjected to the compression process is received from the optical camera 13, a decompression processing on the compressed non-DICOM data and makes the correspondence.

The medical data managing apparatus 11 determines whether there is no transmission request of any other non-DICOM data related to the patient P of the same patient name "T Taro" from the optical camera 13 (step ST16). If it is determined as YES in step ST16, that is, if it is determined that there is no transmission request of any other non-DICOM data related to the patient P of the same patient name "T Taro" from the optical camera 13, the medical data managing apparatus 11 abrogates the SSID "XXXA01" generated by the step ST4 (shown in FIG. 4), and the patient P with the patient name "T Taro" leaves the medical consultation room according to an instruction of the operator D (step ST17).

The medical data managing apparatus 11 may abrogate, in steps ST16 and ST17, the SSID "XXXA01" based on the ID "A01" of the patient P after the preset time elapses. Alternatively, the medical data managing apparatus 11 may abrogate, in steps ST16 and ST17, the SSID "XXXA01" based on the ID "A01" of the patient P by an abrogation instruction input from the input interface 23 (shown in FIG. 3) by an operation of the operator D. Alternatively, the medical data managing apparatus 11 may abrogate, in steps ST16 and ST17, the SSID "XXXA01" based on the ID "A01" of the patient P according to a schedule of the patient P, for example, a next schedule based on the reservation data of examination.

The medical data managing apparatus 11 may request, when abrogating the SSID "XXXA01", the optical camera 13 to delete the non-DICOM data and face image data corresponding to the SSID "XXXA01" stored in the optical camera 13.

If it is determined as NO in step ST16, that is, if it is determined that there is a transmission request of any other non-DICOM data related to the patient P of the same patient name "T Taro" from the optical camera 13, the medical data managing apparatus 11 requests the optical camera 13 to transmit any other non-DICOM data via the communication networks N1 and N2 (step ST13). By repeating the steps ST13 to ST16, multiple non-DICOM data for the same patient can be transmitted from the optical camera 13 to the medical data managing apparatus 11 until the communication network N2, constructed by the step ST7 (shown in FIG. 4), is abrogated in the step ST17.

Following step ST17, the medical data managing apparatus 11 determines, based on the list including the patient information (shown in FIG. 2) acquired by step ST2 (shown in FIG. 4), whether there is no next patient to be entered in the medical consultation room (step ST18). If it is determined as YES in step ST18, that is, if it is determined that there is no next patient, the medical data managing apparatus 11 ends the operation.

If it is determined as NO in step ST18, that is, if it is determined that the next patient is present, the medical data managing apparatus 11 sets the next patient of the name "J Hanako" out of the list including the patient information (shown in FIG. 2) acquired in step ST2, and a patient P of the name "J Hanako" enters the medical consultation room according to an instruction of the operator D (step ST3).

As described above, the medical data managing apparatus 11 repeating steps ST3 (shown in FIG. 4) to ST18 successively generates SSIDs according to the list including the patient information shown in FIG. 2, thereby setting the dynamic SSID.

Proceeding to the description of FIG. 6, the medical data managing apparatus 11 displays, to the display 24, a list screen including a list of the multiple non-DICOM data, temporally stored in memory 22 in step ST15 (shown in FIG. 5), associated with the patient information according to a request from the operator D or a registration manager (not shown) (step ST19). In step ST19, the medical data managing apparatus 11 classifies each non-DICOM data, temporarily stored, into the first non-DICOM data or the second non-DICOM data, and display the first non-DICOM data and the second non-DICOM data on the display 24 so as to be recognizable from each other.

The medical data managing apparatus 11 urges the operator D or the registration manager to finally confirm the suitability of associating each non-DICOM data with the patient information on the list screen, and requests the operator D or the registration manager to delete the second non-DICOM data from the memory 22 (shown in FIG. 3) on the list screen.

Here, a method of classifying each non-DICOM data into the first non-DICOM data or the second non-DICOM data will be described with reference to the medical data managing apparatus 11.

The medical data managing apparatus 11 calculates an association degree of each the non-DICOM data, temporarily stored in step ST15, to multiple past non-DICOM data accumulated in the VNA 14. The medical data managing apparatus 11 classifies each non-DICOM data, temporarily stored, into the first non-DICOM data or the second non-DICOM data according to the calculated association degree.

For example, the medical data managing apparatus 11 acquires the multiple past non-DICOM data (the patient name does not matter), related to the same examination purpose (for example, disease name such as leg burn) as the non-DICOM data, temporarily stored, from the VNA 14, and calculates the association degree of each non-DICOM data as a score, temporarily stored, to the multiple past non-DICOM data. Subsequently, the medical data managing apparatus 11 classifies each non-DICOM data, temporarily stored, into the first non-DICOM data or the second non-DICOM data according to the score of each. For example, in a case where the association degree is expressed by a score of 10 levels (1 to 10 points), the medical data managing apparatus 11 may regard non-DICOM data corresponding to a relatively high score (6 to 10 points) of the association degree as the first non-DICOM data.

Specifically, the medical data managing apparatus 11 calculates, when the examination purpose relating to the non-DICOM data, temporarily stored, is "leg burn", the score of the association degree corresponding to an object (for example, leg) and a photographing angle (for example, frontal view) indicated in each of the non-DICOM data (image data), temporarily stored. The calculation is based on multiple past non-DICOM data (image data), accumulated in the VNA 14, related to the examination purpose "leg burn". The medical data managing apparatus 11 may calculate the score of the association degree of each non-DICOM data, temporarily stored, by machine learning, for example, depth learning (Deep Learning).

Although the case where the association degree is calculated as the score on the basis of the multiple past non-DICOM data related to the same examination purpose as the multiple non-DICOM data, temporarily stored, has been described, it is not limited to that case. For example, the medical data managing apparatus 11 calculates the association degree as the score on the basis of multiple past non-DICOM data corresponding to DICOM data (medical image data) related to the same object as DICOM data corresponding to the non-DICOM data, temporarily stored.

Figure 7:
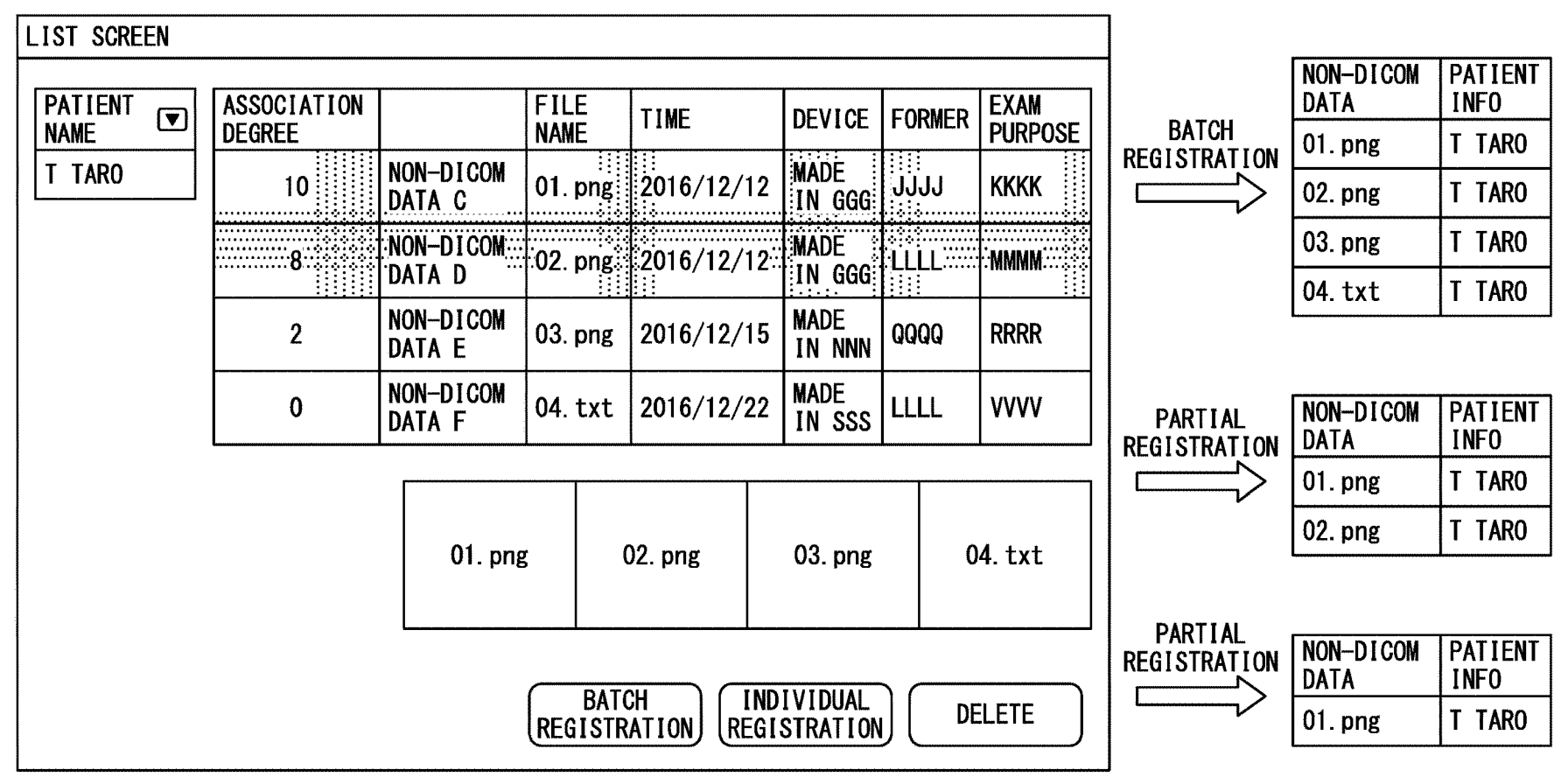

FIG. 7 a diagram for explaining the list screen and a registration result in the medical data managing apparatus 11.

The left side of FIG. 7 shows the list screen of four non-DICOM data temporarily stored in the memory 22 and associated with patient information, for example, patient name "T Taro". The operator D or the registration manager finally determines suitability of registration of the four non-DICOM data associated with the patient name "T Taro" into the VNA 14 while observing the list screen shown in the left side of FIG. 7.

The left side of FIG. 7 shows the list screen of two first non-DICOM data having scores "6 points" or more of the association degree, recognizable to two second non-DICOM data having scores less than "6 points" of the association degree. On the list screen, display modes of the four non-DICOM data are different according to the score of the association degree. For example, only two first non-DICOM data out of four non-DICOM data are highlighted.

According to the list screen on the left side of FIG. 7, the score of the association degree, relating to non-DICOM data indicating leg image data related to the patient of an examination purpose "laceration of upper arm", not indicating a body of the patient, or the like, is low. It is possible to classify that non-DICOM data into the second non-DICOM data and display that fact. Accordingly, it is possible to shorten the time when the operator D or the registration manager instructs deletion of multiple non-DICOM data which is not required to be registered on the list screen. The throughput of the examination is increased since the operator D or the registration manager sequentially confirms the image data having the high score of the association degree.

In addition to, or in place of the classification based on the multiple past non-DICOM data for the same examination purpose, four non-DICOM data may be classified into the first non-DICOM data or the second non-DICOM data on the basis of a comparison result of the four non-DICOM data. For example, the non-DICOM data classified into the second non-DICOM data is image data having image quality poorer than the other image data, image data of an object different from the other image data, or the like. Accordingly, it is possible to shorten the time when the operator D or the registration manager instructs deletion of multiple non-DICOM data which is not required to be registered on the list screen. The throughput of the examination is increased since the operator D or the registration manager sequentially confirms the image data having the high score of the association degree.

On the list screen on the left side of FIG. 7, the operator D or the registration manager may collectively instruct registration of all of the four non-DICOM data, that is all of the first and second non-DICOM data, associated with the patient name "T Taro" as the registering-target into the VNA 14, or may individually instruct registration of a part of the four non-DICOM data associated with the patient name "T Taro" (for example, two first non-DICOM Data) as the registering-target into the VNA 14.

When the operator D or the registration manager collectively instructs the registration of all of the four non-DICOM data associated with the patient name "T Taro", the four non-DICOM data is associated with the patient name "T Taro", respectively, and is registered into the VNA 14, as shown on the right side of FIG. 7. Alternatively, when the operator D or the registration manager partially instructs the registration of one or two of the four non-DICOM data associated with the patient name "T Taro", the one or two non-DICOM data is associated with the patient name "T Taro", respectively, and is registered into the VNA 14, as shown on the right side of FIG. 7.

Returning to the explanation of FIG. 6, in accordance with a request from the operator D or the registration manager (not shown), the medical data managing apparatus 11 registers the registering-target non-DICOM data, which is displayed in step ST19 and to which the patient information is associated, into the VNA 14 via the communication network N1 (step ST20).

It should be noted that the medical data managing apparatus 11 does not necessarily have to perform the final confirmation of the correspondence relationship shown in step ST19. In that case, in step ST20, after a preset time elapses, the medical data managing apparatus 11 registers the non-DICOM data, stored in the memory 22 and associated with the patient information in step ST15 as the registering-target, into the VNA 14 via the communication network N1. Alternatively, in step ST20, in response to a registration request for non-DICOM data from the VNA 14, the medical data managing apparatus 11 registers the non-DICOM data, stored in the memory 22 and associated with the patient information in step ST15 as the registering-target, into the VNA, 14 via the communication network N1.

The medical data managing apparatus 11 registers the non-DICOM data, temporarily stored in the memory 22, as the registering-target into the VNA 14 as the data archive apparatus by using a hypertext transfer protocol (HTTP) communication. However, it is not limited to that case. For example, the medical data managing apparatus 11 converts the non-DICOM data, temporarily stored in the memory 22, into the DICOM format and performs DICOM communication to register the converted DICOM data as the registering-target into a DICOM server (not shown) as the data archive apparatus. An example of the DICOM server is a medical image data system (PACS: Picture Archiving and Communication System).

According to the medical data managing apparatus 11 and the medical data managing system 1, by classifying each non-DICOM data into the first non-DICOM data or the second non-DICOM data and displaying that fact, it is possible to improve the efficiency of selecting the registering-target non-DICOM data into the VNA 14. According to the medical data managing apparatus 11 and the medical data managing system 1, registration of unnecessary non-DICOM data can be prevented.

According to the medical data managing apparatus 11 and the medical data managing system 1, based on the patient information, the SSID is generated and presented to the optical camera 13, and the reference data transmitted from the optical camera 13 via the communication network N2 constructed on the basis of the SSID can be checked against the benchmark data included in the patient information. As a result, only registering-target non-DICOM data, with which appropriate patient information is associated, can be registered into the data archive apparatus such as the VNA 14 or the like.

2. Second Embodiment

Figure 8:
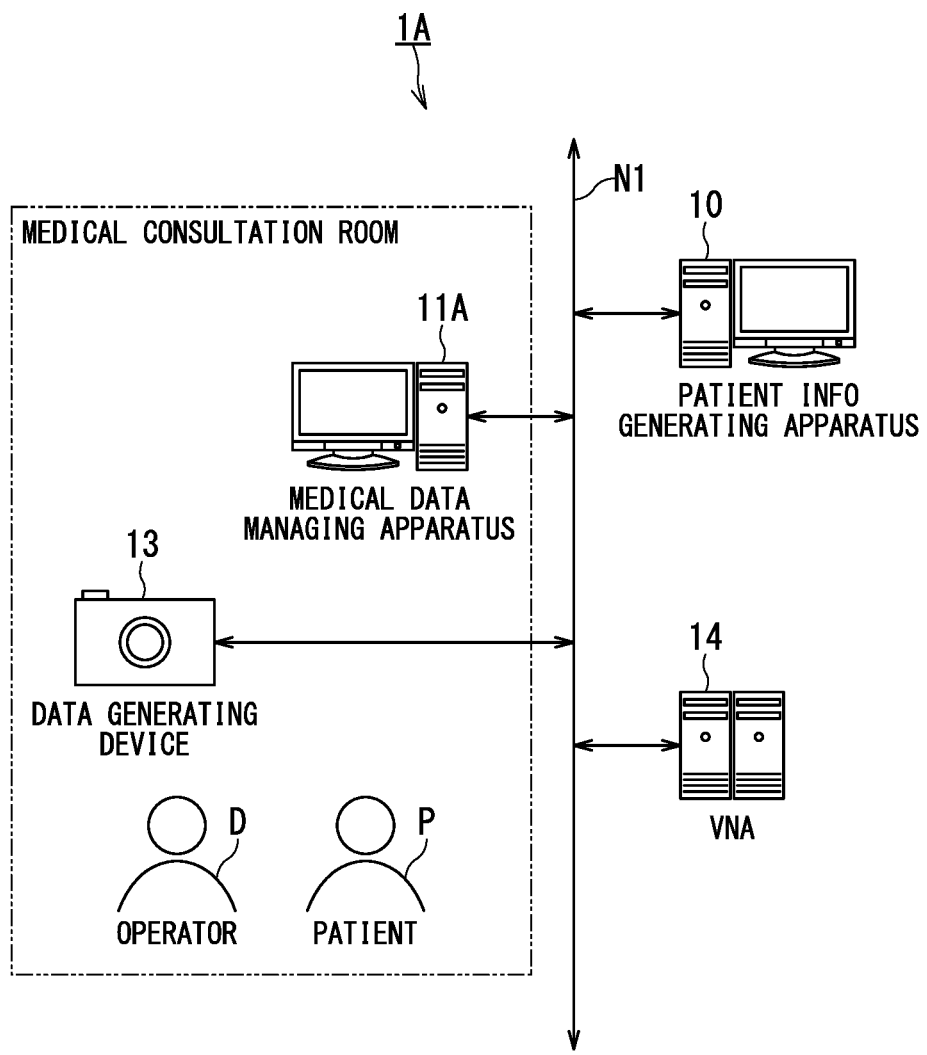
FIG. 8 is a schematic diagram showing the overall configuration of a medical data managing system according to a second embodiment.

FIG. 8 is a schematic diagram showing the overall configuration of a medical data managing system according to a second embodiment.

FIG. 8 shows a medical data managing system 1A according to the second embodiment. The medical data managing system 1A includes the patient information generating apparatus 10, a medical data managing apparatus 11A, the data generating device 13, and the VNA 14. The patient information generating apparatus 10, the medical data managing apparatus 11A, and the VNA 14 are mutually connectable via the communication network N1.

The medical data managing apparatus 11A and the data generating device 13 are provided in a medical consultation room where an operator D such as a doctor, instructing registration of non-DICOM data, and the patient P are present.

In the medical data managing system 1A shown in FIG. 8, the same symbols are assigned to the same components as those of the medical data managing system 1 shown in FIG. 1. The description of these components is omitted.

Figure 9:
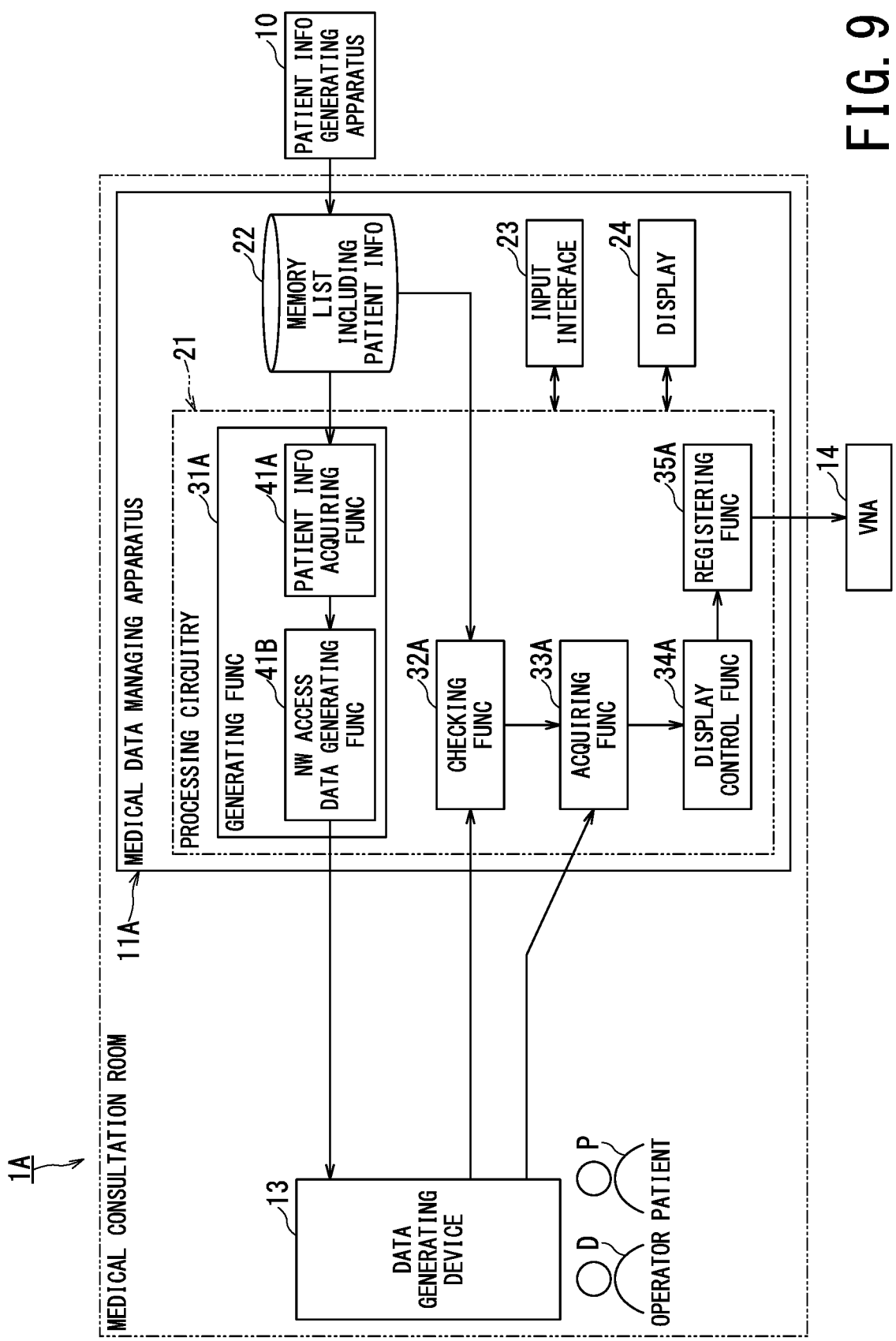
FIG. 9 is a diagram for explaining configurations and functions of the medical data managing system according to the second embodiment.

FIG. 9 is a diagram for explaining configurations and functions of the medical data managing system 1A.

When the processing circuitry 21 of the medical data managing apparatus 11A executes the program, a generating unit (generating function) 31A, a checking unit (checking function) 32A, an acquiring unit (acquiring function) 33A, a display control unit (display control function) 34A, and a registering unit (registering function) 35A are realized. All or part of the functions 31A to 35A may be provided as hardware in the medical data managing apparatus 11A.

The generating function 31A includes a patient information acquiring function 41A and a network access data generating function 42A. The patient information acquiring function 41A includes a function of acquiring the patient information (for example, patient ID) generated in the patient information generating apparatus 10 and stored in the memory 22, similarly to the patient information acquiring function 41 shown in FIG. 3. An example of the patient information is as described above with reference to FIG. 2.

The network access data generating function 42A includes a function of generating network access data based on the patient information acquired by the patient information acquiring function 41A. For example, the network access data generating function 42A generates, as network access data, password data for connecting to the communication network N1, or tag data of a virtual LAN (VLAN). The tag data of the VLAN means data on a tag (identification number) given to a frame flowing through the network in order to configure the group in a VLAN system. Hereinafter, unless otherwise mentioned, the case where the network access data generating function 42A generates the password data as the network access data will be described.

The checking function 32A includes a function of acquiring reference data from the data generating device 13 via the communication network N1 constructed based on the network access data. The checking function 32A is a function of checking the acquired reference data against the benchmark data included in the patient information acquired by the patient information acquiring function 41A.

The acquiring function 33A includes a function of acquiring, when it is determined that the reference data and the benchmark data represent same patient as a result of checking by the checking function 32A, multiple non-DICOM data from the data generating device 13 via the communication network N1.

The display control function 34A includes a function of classifying each non-DICOM data acquired by the acquiring function 33A into the first non-DICOM data or the second non-DICOM data, and of displaying the first non-DICOM data and the second non-DICOM data on the display 24 so as to be recognizable from each other.

The registering function 35A includes a function of registering registering-target non-DICOM data to be registered into the VNA 14, which is a part of the multiple non-DICOM data acquired by the acquiring function 33A. The registering function 35A preferably includes a function of registering the registering-target non-DICOM data into the VNA 14 in association with the patient information.

Details of the above-described functions 31A to 35A will be described later with reference to FIGS. 10 to 12.

Subsequently, an operation of the medical data managing system 1A will be described with reference to FIGS. 10 to 12.

Figure 10:
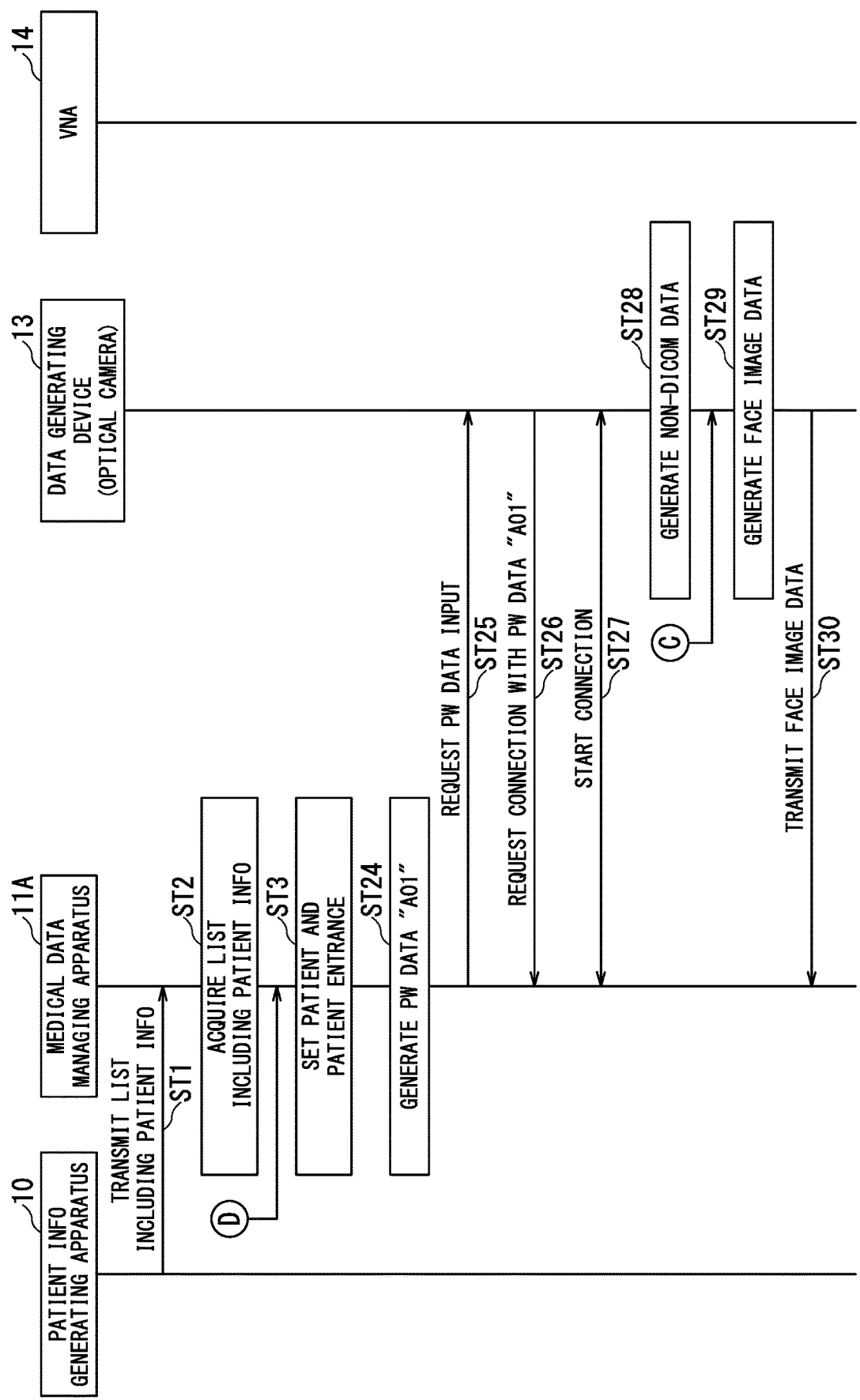
FIG. 10 is a flowchart showing operations example of the medical data managing system according to the second embodiment.
Figure 11:
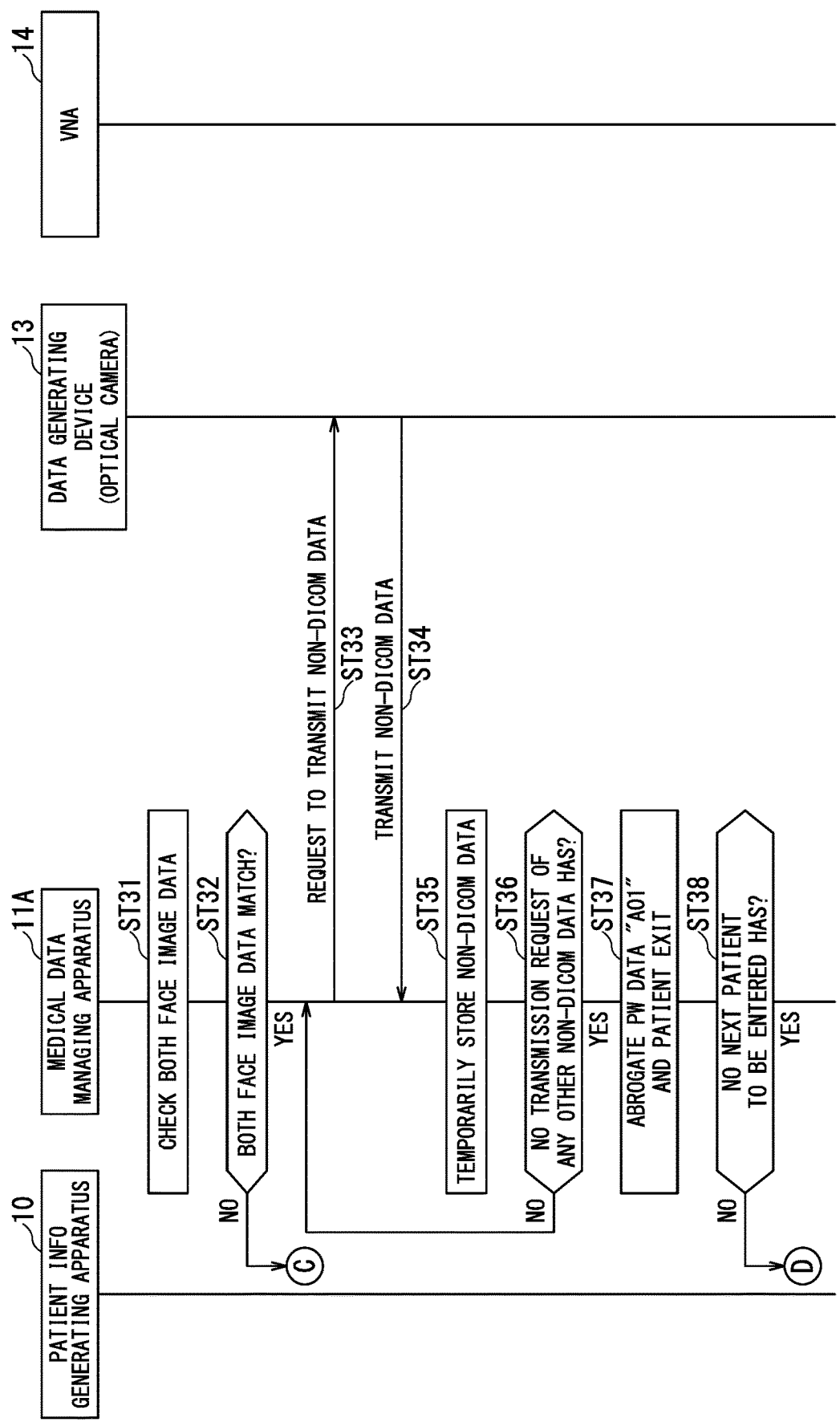
FIG. 11 is a flowchart showing operations example of the medical data managing system according to the second embodiment.
Figure 12:
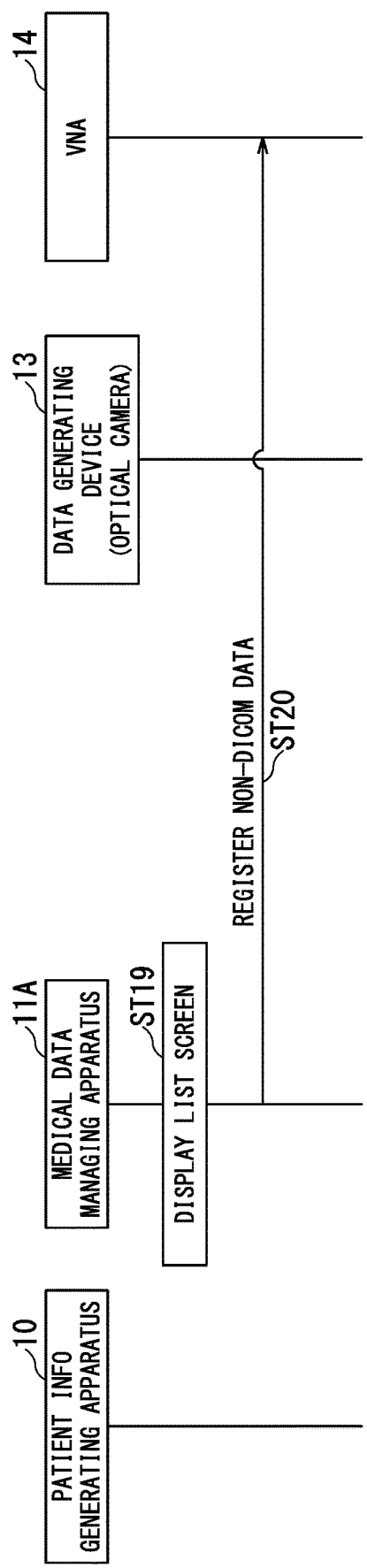
FIG. 12 is a flowchart showing operations example of the medical data managing system according to the second embodiment.

FIGS. 10 to 12 are a flowchart showing an operation example of the medical data managing system 1A.

The operation of the medical data managing system 1A shown in FIGS. 10 to 12 is performed in order to register the registering-target non-DICOM data into the VNA 14 in association with the appropriate patient information, when the registering-target among the multiple non-DICOM data, stored in the optical camera 13, is registered into the VNA 14. Since the patient information is not originally associated with the multiple non-DICOM data stored in the optical camera 13, in the prior art, the operator has performed the association by manual operations.

In FIGS. 10 to 12, the same symbols are assigned to the same steps as those shown in FIGS. 4 to 6. The description of these components is omitted.

As shown FIG. 10, the medical data managing apparatus 11A generates password data to connect the communication network N1 as the network access data based on the patient information on the patient P with the patient name "T Taro" set in step ST3 (step ST24). In step ST24, the medical data managing apparatus 11A generates the password data including "A01" based on the ID "A01" as the patient information on the patient P with the patient name "T Taro".

For example, in step ST24, the medical data managing apparatus 11A generates, as the password data including "A01", a password data "A01" including only the ID "A01", a password data "XXXA01" including the default "XXX" and the ID "A01". Hereinafter, the case where the medical data managing apparatus 11A generates the password data "A01" including only the ID "A01" in step ST24 will be described.

The medical data managing apparatus 11A requests the optical camera 13 to input password data (step ST25). By using a serial number or the like of the optical camera 13, a device accessible to the network may be limited in advance.

The operator D inputs, as required in step ST25, password data "A01" to the optical camera 13, the password data being based on the ID "A01", related to the patient P of the patient name "T Taro" set on the display 24 set in step ST3, the patient P being in the medical consultation room. The optical camera 13 requests a connection to the communication network N1 with the password data "A01" by an operation of the operator D (step ST26).

The operator D knows in advance that the ID related to the patient P is password data. As a result, the optical camera 13 is connected to the medical data managing apparatus 11A via the communication network N1 constructed based on the password data "A01" (step ST27).

According to the connection in steps ST24 to ST27 described above, appropriateness of the patient information to be associated with the non-DICOM data is, when connecting the optical camera 13 to the medical data managing apparatus 11A, is assigned to the operator D using the password data. Therefore, when the optical camera 13 is connected to the medical data managing apparatus 11A, it is possible to prevent mistakes in the patient information at the time of the association, which was a problem in the conventional technique.

Following step ST27, the operator D uses the optical camera 13 to photograph an object such as an affected part of the patient P with the patient name "T Taro" who is in the medical consultation room, and as a result, the optical camera 13 generates multiple non-DICOM data related to the patient P with the patient name "T Taro" (step ST28). It should be noted that the step ST28 may be performed before the communication network N1 is constructed in step ST27.

The operator D uses the optical camera 13 to photograph a face of the patient P with the patient name "T Taro" who is in the medical consultation room, and as a result, the optical camera 13 generates face image data related to the patient P with the patient name "T Taro" (step ST29). Here, the operator D uses, when the reference data shown in FIG. 2 is bar code data, a bar code reader function of the optical camera 13 to read a bar code of a ribbon attached to a wrist of the patient P with the patient name "T Taro" who is in the medical consultation room, and as a result, the optical camera 13 generates the bar code data related to the patient P with the patient name "T Taro" (step ST29).

The optical camera 13 transmits the face image data, related to the patient P with the patient name "T Taro" generated in step ST29, to the medical data managing apparatus 11 via the communication network N1 constructed based on the password data "A01" (step ST30). The optical camera 13 transmits, when the reference data is the tag data of the VLAN, the face image data only to the medical data managing apparatus 11A having the same tag data by the switch.

Turning to the explanation of FIG. 11, the medical data managing apparatus 11A checks the face image data transmitted in step ST30 against the face image data included in the patient information relating to the patient name "T Taro" set in step ST3 (step ST31). Here, the checking of two face image data can be realized by, for example, a pattern matching using feature point extraction (including character string matching), or the like.

The medical data managing apparatus 11A determines whether or not the face image data transmitted in step ST30 matches the face image data set in step ST3, or whether or not both face image data represent same patient (step ST32). That is, the medical data managing apparatus 11A matches the face image data, corresponding to the non-DICOM data relating to the patient in the medical consultation room, with the face image data, included in the patient information to be associated with the non-DICOM data, as a result, it is determined whether or not the non-DICOM data should be associated with the patient information.

If it is determined as YES in step ST32, that is, if it is determined that the transmitted face image data matches the face image data included in the patient information, the medical data managing apparatus 11A requests the optical camera 13 to transmit the non-DICOM data via the communication network N1 (step ST33).

If it is determined as NO in step ST32, that is, if it is determined that the transmitted face image data does not match the face image data included in the patient information, the medical data managing apparatus 11A notifies that fact to the optical camera 13. Then, the optical camera 13 again generates face image data on the patient P with the patient name "T Taro" as the reference data (step ST29 in FIG. 10).

Following step ST33, the optical camera 13 transmits, in accordance with an operation of the operator D, the non-DICOM data generated in step ST28 to the medical data managing apparatus 11A via the communication network N1 (step ST34). The optical camera 13 transmits, when the reference data is the tag data of the VLAN, the face image data only to the medical data managing apparatus 11A having the same tag data by the switch. Here, the optical camera 13 may perform the predetermined process on the non-DICOM data, and transmit the processed non-DICOM data to the medical data managing apparatus 11A via the communication network N1. The optical camera 13 applies at least one of the encryption processing and the compression processing to the non-DICOM data.

The medical data managing apparatus 11A is able to determine, when the non-DICOM data is transmitted from the optical camera 13, the suitability of the patient information to associate with the non-DICOM data generated by the optical camera 13, as shown in steps ST29 (shown in FIG. 10) to ST34. Therefore, it is possible to prevent mistakes in the patient information at the time of the association, which was a problem in the conventional technique, when the optical camera 13 is connected to the medical data managing apparatus 11A (steps ST24 to ST27) and when the non-DICOM data is transmitted (steps ST30 to ST34).

The medical data managing apparatus 11A receives the non-DICOM data transmitted in step ST34, and temporarily stores the non-DICOM data into the memory 22 in association with the patient information corresponding to the password data "A01" generated by step ST24 (shown in FIG. 10) (step ST35). Here, the medical data managing apparatus 11A performs, when the non-DICOM data subjected to the encryption process is received from the optical camera 13, a decryption process on the encrypted non-DICOM data and makes the correspondence. The medical data managing apparatus 11A performs, when the non-DICOM data subjected to the compression process is received from the optical camera 13, a decompression processing on the compressed non-DICOM data and makes the correspondence.

The medical data managing apparatus 11A determines whether there is no transmission request of any other non-DICOM data related to the patient P of the same patient name "T Taro" from the optical camera 13 (step ST36). If it is determined as YES in step ST36, that is, if it is determined that there is no transmission request of any other non-DICOM data related to the patient P of the same patient name "T Taro" from the optical camera 13, the medical data managing apparatus 11A abrogates the password data "A01" generated by the step ST24 (shown in FIG. 10), and the patient P with the patient name "T Taro" leaves the medical consultation room according to an instruction of the operator D (step ST37).

The medical data managing apparatus 11A may abrogate, in steps ST36 and ST37, the password data "A01" based on the ID "A01" of the patient P after the preset time elapses. Alternatively, the medical data managing apparatus 11A may abrogate, in steps ST36 and ST37, the password data "A01" based on the ID "A01" of the patient P by an abrogation instruction input from the input interface 23 (shown in FIG. 9) by an operation of the operator D. Alternatively, the medical data managing apparatus 11A may abrogate, in steps ST36 and ST37, the password data "A01" based on the ID "A01" of the patient P according to a schedule of the patient P, for example, a next schedule based on the reservation data of examination.

The medical data managing apparatus 11A may request, when abrogating the password data "A01", the optical camera 13 to delete the non-DICOM data and face image data corresponding to the password data "A01" stored in the optical camera 13.

If it is determined as NO in step ST36, that is, if it is determined that there is a transmission request of any other non-DICOM data related to the patient P of the same patient name "T Taro" from the optical camera 13, the medical data managing apparatus 11A requests the optical camera 13 to transmit any other non-DICOM data via the communication network N1 (step ST33). By repeating the steps ST33 to ST36, multiple non-DICOM data for the same patient can be transmitted from the optical camera 13 to the medical data managing apparatus 11A until the communication network N1, constructed by the step ST27 (shown in FIG. 10), is abrogated in the step ST37.

Following step ST37, the medical data managing apparatus 11A determines, based on the list including the patient information (shown in FIG. 2) acquired by step ST2 (shown in FIG. 10), whether there is no next patient to be entered in the medical consultation room (step ST38). If it is determined as YES in step ST38, that is, if it is determined that there is no next patient, the medical data managing apparatus 11A ends the operation.

If it is determined as NO in step ST38, that is, if it is determined that the next patient is present, the medical data managing apparatus 11A sets the next patient of the name "J Hanako" out of the list including the patient information (shown in FIG. 2) acquired in step ST2, and a patient P of the name "J Hanako" enters the medical consultation room according to an instruction of the operator D (step ST3 in FIG. 10).

As described above, the medical data managing apparatus 11A repeating steps ST3 (shown in FIG. 10) to ST38 successively generates passwords according to the list including the patient information shown in FIG. 2, thereby setting the dynamic password.

Proceeding to the description of FIG. 12, the medical data managing apparatus 11A displays, to the display 24, a list screen including a list of the multiple non-DICOM data, temporally stored in memory 22 in step 35 (shown in FIG. 11), associated with the patient information according to a request from the operator D (step ST19). The medical data managing apparatus 11A registers, according to a request of the operator D, the registering-target non-DICOM data associated with the patient information into the VNA 14 via the communication network N1 (step ST20). The operations of steps ST19 and ST20 by the medical data managing apparatus 11A are the same as the operations of steps ST19 and ST20 by the medical data managing apparatus 11 shown in FIG. 6, and thus the description thereof will be omitted.

A method in the medical data managing apparatus 11A that connects the optical camera 13 to the communication network N1 by wire using the password data is applied to the medical data managing apparatus 11 (shown in FIG. 1 and the like) that wirelessly connects the optical camera 13 to the communication network N1. In that case, the medical data managing apparatus 11 does not need to generate the SSID according to the patient P as appropriate, and appropriately generate the password data as the encryption key depending on the patient P. The medical data managing apparatus 11 can wirelessly connect the optical camera 13 to the communication network N1 by a combination of a fixed SSID and variable password data.

According to the medical data managing apparatus 11A and the medical data managing system 1A, by classifying each non-DICOM data into the first non-DICOM data or the second non-DICOM data and displaying that fact, it is possible to improve the efficiency of selecting the registering-target non-DICOM data into the VNA 14. According to the medical data managing apparatus 11A and the medical data managing system 1A, registration of unnecessary non-DICOM data can be prevented.

According to the medical data managing apparatus 11A and the medical data managing system 1A, based on the patient information, the password data is generated and presented to the optical camera 13, and the reference data transmitted from the optical camera 13 via the communication network N1 constructed on the basis of the password data can be checked against the benchmark data included in the patient information. As a result, only registering-target non-DICOM data, with which appropriate patient information is associated, can be registered into the data archive apparatus such as the VNA 14 or the like.

3. Third Embodiment

Figure 13:
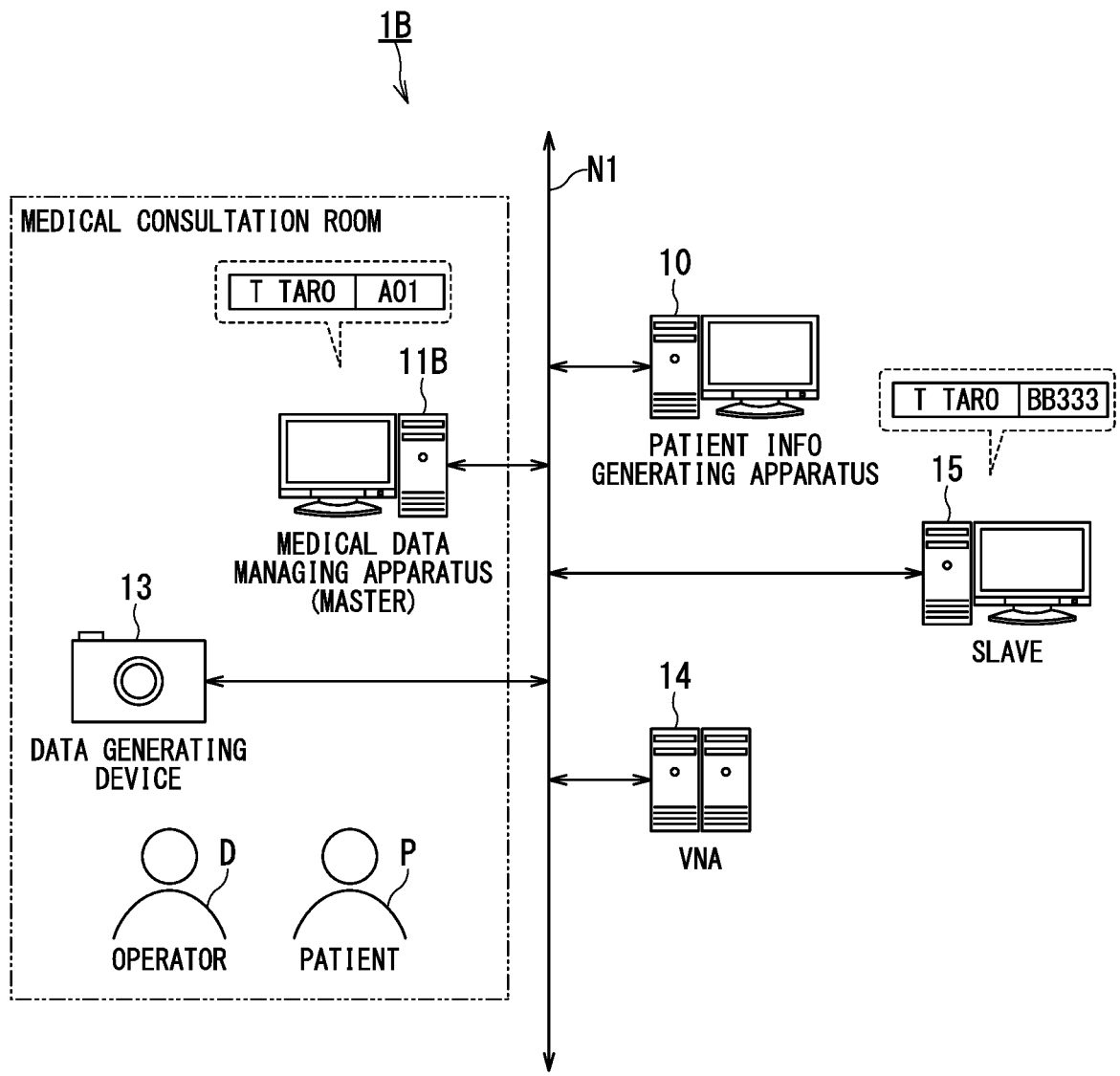
FIG. 13 is a schematic diagram showing the overall configuration of a medical data managing system according to a third embodiment.

FIG. 13 is a schematic diagram showing the overall configuration of a medical data managing system according to a third embodiment.

FIG. 13 shows a medical data managing system 1B according to the third embodiment. The medical data managing system 1B is assumed to share data within a group adopting the master-slave system or among hospitals within a certain area. The master-slave system means, when devices cooperatively operate, a scheme in which roles are shared between "master" and "slave", the "master" managing control and operation of the devices, and "slave" operating under unilateral control of the master.

The medical data managing system 1B includes the patient information generating apparatus 10, a medical data managing apparatus (master) 11B, the data generating device (for example, optical camera) 13, the VNA 14, and a slave 15. The master 11B and the slave 15 are provided in different hospitals. The patient information generating apparatus 10, the medical data managing apparatus 11B, the data generating device 13, and the VNA 14 are mutually connectable via the communication network N1 such as a wired LAN.

In the medical data managing system 1B shown in FIG. 13, the same symbols are assigned to the same components as those of the medical data managing system 1 shown in FIG. 1 and the medical data managing system 1A shown in FIG. 8. The description of these components is omitted.

The medical data managing apparatus 11B has the same configurations and functions as those of the medical data managing apparatus 11 shown in FIGS. 1 and 3, and the configurations and functions of the medical data managing apparatus 11A shown in FIGS. 8 and 9. Furthermore, the medical data managing apparatus 11B functions as a master for the slave 15.

The slave 15 includes processing circuitry, a memory, an input interface, and a display (not shown). The memory of the slave 15 stores the non-DICOM data and the like acquired at a second hospital. Furthermore, the slave 15 functions as a slave for the master 11B.

In the medical data managing system 1B, the slave 15 of the second hospital determines, when the communication network N1 is constructed based on the password data "A01" based on the patient ID "A01" for the master 11B of the first hospital, whether or not to own the non-DICOM data relating to the patient ID "BB333" associated with the patient ID "A01" of the first hospital (step ST7 in FIG. 4 and step ST27 in FIG. 10). The slave 15 transmits, when determining that the second hospital owns non-DICOM data related to the patient ID "BB333", the non-DICOM data related to the patient ID "A01" to the master 11B. The master 11B registers the non-DICOM data transmitted from the slave 15 into the VNA 14 in association with the patient information on the patient ID "A01".

As described above, the patient ID of the patient name "T Taro" owned by the second hospital having the slave 15 is generally different from the patient ID "A01" of the patient name "T Taro" possessed by the first hospital provided with the master 11B. For example, as shown in FIG. 13, while the patient ID of the patient name "T Taro" owned by the first hospital having the master 11B is "A01", the patient name "T Taro" owned by the second hospital having the slave 15 is "BB333". The connection of patient IDs corresponding to the same patient name can be achieved by techniques of PIX (Patient Identifier Cross-referencing)/PDQ (Patient Demographics Query) and MPI (Master Patient Index), using a table or the like in which the patient IDs are associated with each other in advance. The PIX/PDQ is a mechanism for identifying patients, and is a mechanism for issuing and managing unique ID in the community with respect to patient IDs managed in multiple hospitals.

According to at least one embodiment described above, a selecting operation of non-DICOM data to be registered in the data archive apparatus can be made more efficient. Further, according to at least one embodiment, the non-DICOM data associated with appropriate patient information can be registered in the data archive apparatus.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical data managing apparatus, connected via a communication network to (1) a data generating device owning reference data for verification and multiple non-DICOM (Digital Imaging and Communications in Medicine) data and (2) a separate data archive apparatus, the medical data managing apparatus comprising:
   a display; and
   processing circuitry configured to:
      generate network access data based on patient information of a patient,
      acquire the reference data from the data generating device via a communication network constructed based on the network access data, and check the reference data against benchmark data included in the patient information,
      acquire, when it is determined that the reference data and the benchmark data represent a same patient as a result of the check, the multiple non-DICOM data from the data generating device via the constructed communication network,
      classify each of the multiple non-DICOM data into first non-DICOM data to be registered in the separate data archive apparatus or second non-DICOM data not needed to be registered in the separate data archive apparatus, and
      display on the display the first non-DICOM data and the second non-DICOM data in different display modes such that the first non-DICOM data is visually distinguishable from the second non-DICOM data.

2. The medical data managing apparatus according to claim 1, wherein the processing circuitry is configured to
   calculate association degree of each of the multiple non-DICOM data to past non-DICOM data accumulated in the data archive apparatus, and
   classify each of the multiple non-DICOM data into the first non-DICOM data or the second non-DICOM data according to the association degree.

3. The medical data managing apparatus according to claim 2, wherein the processing circuitry is configured to
   display, on the display, a screen including the multiple non-DICOM data as elements, and
   control, in the screen, display modes of the multiple non-DICOM data so as to be different according to the association degree.

4. The medical data managing apparatus according to claim 1, wherein the classified second non-DICOM data includes image data whose image quality is worse than other image data or indicates image data of an object different from other image data.

5. The medical data managing apparatus according to claim 1, wherein
   the processing circuitry is configured to perform, when it is determined that the reference data and the benchmark data represent the same patient as the result of the check, a predetermined processing on multiple unprocessed non-DICOM data to acquire multiple processed non-DICOM data as the multiple non-DICOM data from the data generating device via the constructed communication network.

6. The medical data managing apparatus according to claim 5, wherein
   the processing circuitry is configured to acquire the multiple processed non-DICOM data subjected to at least one of an encryption processing and a compression processing as the predetermined processing on the multiple unprocessed non-DICOM data.

7. The medical data managing apparatus according to claim 1, wherein the processing circuitry is configured to request, when abrogating the network access data, the data generating device to delete the multiple non-DICOM data and the reference data corresponding to the network access data stored in the data generating device.

8. The medical data managing apparatus according to claim 1, wherein the processing circuitry is further configured to register, according to a registration instruction from an input interface, the first non-DICOM data or a part of multiple first non-DICOM data as registering-target non-DICOM data into the data archive apparatus.

9. The medical data managing apparatus according to claim 8, wherein the data archive apparatus comprises a Vendor Neutral Archive or a DICOM server, and the processing circuitry is configured to register the first non-DICOM data or the part of the multiple non-DICOM data as registering-target non-DICOM data into the data archive apparatus.

10. A medical data managing system comprising:
    a data generating device owning reference data for verification and multiple non-DICOM data;
    a medical data managing apparatus;
    a data archive apparatus separate from the medical data managing apparatus; and
    a communication network for interconnecting the data generating device, the medical data managing apparatus, and the data archive apparatus, wherein the medical data managing apparatus comprises
a display and processing circuitry configured to:
generate network access data based on patient information of a patient;
acquire the reference data from the data generating device via a communication network constructed based on the network access data, and check the reference data against benchmark data included in the patient information;
acquire, when it is determined that the reference data and the benchmark data represent a same patient as a result of the check, the multiple non-DICOM data from the data generating device via the constructed communication network,
classify each of the multiple non-DICOM data into first non-DICOM data to be registered in the data archive apparatus or second non-DICOM data not needed to be registered in the data archive apparatus, and
display on the display the first non-DICOM data and the second non-DICOM data in different display modes such that the first non-DICOM data is visually distinguishable from the second non-DICOM data.

11. The medical data managing system according to claim 10, wherein the processing circuitry is configured to
calculate association degree of each of the multiple non-DICOM data to past non-DICOM data accumulated in the data archive apparatus, and
classify each of the multiple non-DICOM data into the first non-DICOM data or the second non-DICOM data according to the association degree.

12. The medical data managing system according to claim 11, wherein the processing circuitry is configured to
display, on the display, a screen including the multiple non-DICOM data as elements, and
control, in the screen, display modes of the multiple non-DICOM data so as to be different according to the association degree.

13. The medical data managing system according to claim 10, wherein the classified second non-DICOM data includes image data whose image quality is worse than other image data or indicates image data of an object different from other image data.

14. The medical data managing system according to claim 10, wherein
the medical data managing apparatus, the data archive apparatus, and an access point are connected via a wired communication network, and
the data generating device is connected to the access point via a wireless communication network.

15. The medical data managing system according to claim 14, wherein
the processing circuitry is configured to
generate a service set identifier (SSID) as the network access data based on the patient information, and provide the data generating device with the SSID,
acquire the reference data from the data generating device via the wireless communication network constructed based on the SSID, and
acquire the multiple non-DICOM data from the data generating device via the constructed wireless communication network.

16. The medical data managing system according to claim 14, wherein
the processing circuitry is configured to
generate password data as the network access data based on the patient information,
acquire the reference data from the data generating device via the communication network constructed based on the password data, and
acquire the multiple non-DICOM data from the data generating device via the constructed communication network.

17. The medical data managing system according to claim 10, wherein the medical data managing apparatus, the data archive apparatus, and the data generating device are connected via a wired communication network.

18. The medical data managing system according to claim 17, wherein
the processing circuitry is configured to
generate tag data of a virtual local area network (VLAN) as the network access data based on the patient information,
acquire the reference data from the data generating device via the wired communication network constructed based on the tag data, and
acquire the multiple non-DICOM data from the data generating device via the constructed wired communication network.

19. The medical data managing system according to claim 10, wherein
the processing circuitry is configured to acquire the patient information via network from hospital information systems (HIS), radiology information systems (RIS), a medical reception apparatus, a medical image diagnostic device, an electronic medical chart server, or a modality work-list management (MWM) server connected via the communication network.

20. The medical data managing system according to claim 10, wherein the data archive apparatus comprises a Vendor Neutral Archive or a DICOM server and the processing circuitry is further configured to register, using a hypertext transfer protocol (HTTP) communication, the first non-DICOM data or a part of multiple first non-DICOM data as registering-target non-DICOM data into the data archive apparatus.

21. The medical data managing system according to claim 20, wherein, when the data archive apparatus is a DICOM server, the processing circuitry is configured to convert the registering-target non-DICOM data into a DICOM format and perform DICOM communication to register the converted registering-target DICOM data into the DICOM server.

* * * * *